(12) United States Patent
Byon et al.

(10) Patent No.: US 8,920,869 B2
(45) Date of Patent: Dec. 30, 2014

(54) OSSEOINDUCTIVE METAL IMPLANTS FOR A LIVING BODY AND PRODUCING METHOD THEREOF

(75) Inventors: Eung-Sun Byon, Changwon-si (KR);
Yong-Soo Jeong, Changwon-si (KR);
Jong-Kuk Kim, Changwon-si (KR);
Young-Taeg Sul, Gothenberg (SE);
Beom-Seok Chang, Gangneung-si (KR);
Lee-Ra Cho, Gangneung-si (KR)

(73) Assignee: Korea Institute of Machinery and Materials, Daejon (KR)

( * ) Notice: Subject to any disclaimer, the term of this patent is extended or adjusted under 35 U.S.C. 154(b) by 1520 days.

(21) Appl. No.: 11/578,178

(22) PCT Filed: Mar. 31, 2005

(86) PCT No.: PCT/KR2005/000947
§ 371 (c)(1),
(2), (4) Date: Jan. 7, 2008

(87) PCT Pub. No.: WO2006/004297
PCT Pub. Date: Jan. 12, 2006

(65) Prior Publication Data
US 2009/0017087 A1    Jan. 15, 2009

(30) Foreign Application Priority Data
Apr. 26, 2004  (KR) .................. 10-2004-0028550

(51) Int. Cl.
*A61F 2/00* (2006.01)
*A61L 27/30* (2006.01)
(Continued)

(52) U.S. Cl.
CPC ....... *C25D 11/34* (2013.01); *A61F 2310/00023* (2013.01); *A61L 27/306* (2013.01); *A61F 2310/00616* (2013.01); *C25D 11/26* (2013.01); *A61F 2310/00622* (2013.01); *A61F 2/30767* (2013.01); *A61F 2310/00029* (2013.01); *A61F 2310/00598* (2013.01); *B08B 7/0035* (2013.01);
*A61F 2310/00796* (2013.01); *C23C 8/10* (2013.01); *A61F 2310/00628* (2013.01); *A61L 27/06* (2013.01); *A61F 2002/3097* (2013.01); *A61F 2002/30929* (2013.01); *A61F 2/3094* (2013.01); *A61F 2310/00634* (2013.01); *A61F 2310/00017* (2013.01); *A61C 8/0012* (2013.01); *A61F 2002/30925* (2013.01); *A61F 2002/30981* (2013.01); *A61F 2310/00089* (2013.01)
USPC .................... 427/2.27; 427/2.26; 424/422

(58) Field of Classification Search
USPC ................................ 424/422; 427/2.26, 2.27
See application file for complete search history.

(56) References Cited

U.S. PATENT DOCUMENTS

| | | | |
|---|---|---|---|
| 4,145,764 A | 3/1979 | Suzuki et al. | |
| 5,558,718 A * | 9/1996 | Leung .................. | 118/723 E |

(Continued)

FOREIGN PATENT DOCUMENTS

| | | |
|---|---|---|
| EP | 0 232 791 | 1/1987 |
| JP | 5-5703 | 1/1993 |

(Continued)

OTHER PUBLICATIONS

Porous Coatings for Improved Implant Life—Total Hip Replacements, Materials World, vol. 11, No. 2, p. 16-17 Feb. 2003.*

(Continued)

*Primary Examiner* — Rebecca Lee
(74) *Attorney, Agent, or Firm* — Birch, Stewart, Kolasch & Birch, LLP (57) ABSTRACT

This invention provides an Osseo-inductive metal implant for a living body and the producing method thereof and, more particularly, the Osseo-inductive metal implant for a living body according to the present invention is produced by forming, on the surface of the metal implant, the layer of metal oxide and the layer of bio-active material injected.

7 Claims, 6 Drawing Sheets

(51) Int. Cl.
  *C25D 11/26* (2006.01)
  *A61F 2/30* (2006.01)
  *B08B 7/00* (2006.01)
  *C23C 8/10* (2006.01)
  *A61L 27/06* (2006.01)
  *C25D 11/34* (2006.01)
  *A61L 33/02* (2006.01)
  *A61C 8/00* (2006.01)

(56) References Cited

U.S. PATENT DOCUMENTS

| | | | |
|---|---|---|---|
| 5,603,338 | A | 2/1997 | Beaty |
| 5,876,453 | A | 3/1999 | Beaty |
| 5,972,163 | A * | 10/1999 | Haji .................. 156/345.54 |
| 6,280,789 | B1 * | 8/2001 | Rey et al. .................. 427/2.27 |

FOREIGN PATENT DOCUMENTS

| | | |
|---|---|---|
| JP | 5-57012 | 3/1993 |
| JP | 10-503108 | 3/1998 |
| JP | 10-179718 | 7/1998 |
| JP | 10-243997 | 9/1998 |
| JP | 10243997 A | 9/1998 |
| JP | 2001-452 | 1/2001 |
| JP | 2003-325553 | 11/2003 |
| WO | WO 02 096475 | 12/2002 |
| WO | WO 2004 010887 | 2/2004 |

OTHER PUBLICATIONS

Machine translation of JP 10243997.*
Young-Taeg Sui, On the Bone Response to Oxidized Titanium Implants: The role of microporous structure and chemical compositions of the surface oxide in enhanced osseointegration, dated 2002.
H. Oonishi et al., Degradation/resorption in bioactive ceramics in orthopaedics, Handbook of Biomaterial Properties, dated 1998.
R. Z. LeGeros et al., Significance of the Porosity and Physical Chemistry of Calcium Phosphate Ceramics, Biodegradation—Bioresorption, Annals New York Academy of Sciences, vol. 523(a), pp. 268-271, Jun. 1988.
Moussa Hamadouche et al., Long-term in vivo bioactivity and degradability of bulk sol-gel bioactive glasses, Bulk Sol-Gel Glasses, pp. 560-566, dated Aug. 8, 2000.
Fujibayashi et al: "Osteoinduction of porous bioactive titanium metal", In: Biomaterials, Feb. 2004, vol. 25(3), pp. 443-450.
Lacefield: Materials characteristics of uncoated/ceramic-coated implant materials, In: Advv. Dent. Res., 1999, vol. 13, pp. 21-26.

* cited by examiner

Base Metal (b)

Base Metal

OSSEOINDUCTIVE METAL IMPLANTS FOR A LIVING BODY AND PRODUCING METHOD THEREOF

TECHNICAL FIELD

The present invention relates to Osseo-inductive metal implants for a living body and the producing method thereof. For further details, on the surface of the metal implant, the layer of metal oxide and the layer of bio-active material injected are to be formed for the purpose of implanting in the human body.

BACKGROUND ART

Previously, a technique mechanical processing a surface roughly on a metal implant to promote the osseous bonding force (U.S. Pat. No. 5,876,453) and further a technique producing the implant surface roughly by chemically etching a surface by blasting using ceramic particles or using a mixture of sulfuric acid and hydrochloric acid (U.S. Pat. No. 5,603,338) are disclosed.

According to a recent reference (Sul PhD thesis, Gothenburg Univ. Sweden 2002), a technique promoting a biochemical bonding by improving the chemical components of the implant surface is required, than metal implants free from said background art, i.e. a morphological improvement of the implant-surface.

As for improving the chemical components of the implant surface, a method melting ceramic particles at high temperature and injecting the melted ceramic on the implant surface so as to reform a Osseo-inductive surfaces (U.S. Pat. No. 4,145,764), and a method pressing a living-active ceramics particle such as a hydroxyapatite on the implant surface (JP-A 2001-00452), a method initiating ceramics which similar to bone components on a titanium implant surface (JP-A 1993-05703), a method forming a calcium titanate layer to improve binding ability outside implants and forming a calcium phosphate layer with excellent bone bonding force on the layer (JP-A 1993-057012), a method performing a thermal spray coating with a bio-compatible calcium phosphate on the implant surface and performing both pressurized water and polarization treatment (JP-A 2003-325553), and the like are already disclosed.

DISCLOSURE OF INVENTION

Technical Problem

The said hydroxyapatite ceramics have been used extensively due to excellent biocompatibility, quick recovery and high bone bonding avidity. However, after long time goes in body, a problem of degradation or resorption would happen. Furthermore, as for defects of implant which has a coating with calcium phosphate, hydroxyapatite, bio glass, bio ceramics and the like, it was reported that, in case the metal implants are clinically applied for a long time, delamination of the coated materials from the implant or the surface or inside of the coating material, and chronic inflammation of a bone tissue in the neighborhood of the implant by biodegradation and resorption arising from biological effects (LeGeros 1993, Oonishi & Oonmamiuda 1998, Hamadouche et al. 2001) make the possibility of successful transplanting fall down (Albrektsson 1998).

Moreover, a method implanting hydroxyapatite onto the surface by settling down the implants in the mixed electrolyte solution of calcium ion and phosphate ion, and contacting anode and cathode alternatively (JP-A 1998-503108), a method anodizing the surface of implants by spark discharge in an electrolyte including calcium ions (EP 0232791), a method forming a coating film having each phase of titanite and alkali titanite on the surface by baking after settling down base titanium in a alkali solution and calcium ions respectively (JP-A 1998-179718), a method settling down in alkali solution by heat treating after ion implanting calcium on a base titanium surface (JP-A 1998-243997) and the like are disclosed. These methods such as implantation, anodic oxidation and baking etc do not form interface between the implant and coated films, and biodegradation or resorption does not take place even if long time elapses in a living body. However, it takes much time in recovery and it is heavy burden on the patient.

Technical Solution

The purpose of present invention is providing Osseo-inductive metal implants, composed of including the layer of metal oxide and the layer of bio-active material for a living body and the producing method thereof, so as to have high bone bonding force and quick recovery time by implanting various types of bio-active material on the surface of metal implant to be operated to various patients in the fields of dentistry, orthopedic surgery, ENT, mandibulofacial surgery, plastic surgery and the like to strengthen the function of Osseo integration.

The present invention relates to Osseo-inductive metal implants for a living body is characterized in a layer of a metal oxide and a layer of a bio-active material formed in this order on the metal implants surface.

The said metal implants according to the present invention may be applied without any limitation. Preferably, titanium of commercial purity or some titanium alloys comprising any one or more of Al, V, Na, Mg, P, Nb, Zr, Sn, Pt and Ta of 0.1 to 15% by weight added thereto. Said titanium of commercial purity is called that with purity of 98% to 99% including impurities of nitrogen, carbon, hydrogen, oxygen, iron, aluminum and the like of 1 to 2% by weight. Furthermore, except said titanium alloys, cobalt-chromium alloy, stainless steel (314, 316, 316L 22-13-5 Stainless Steel) and zirconium alloy and the like may be applied. Then, a cobalt-chromium alloy means the one comprising any one or more of Mo, W, Ni, Mn, C, Si and Fe of 0.1 to 45% by weight added to cobalt-chromium. A stainless steel means the one comprising Ni of 10 to 16%, Cr of 10 to 18%, Mo of 2 to 3% by weight and any one or more of C, Si, Mn, P and S of 0.01 to 2% by weight added to Fe of purity of 60 to 73%, or the one comprising Cr of 20 to 24%, Ni of 11 to 14%, Mn of 4 to 6%, Mo of 1 to 3%, Nb of 0.1 to 0.3%, N of 0.2 to 0.4%, V of 0.1 to 0.3% by weight and any one or more of C, Si, P and S of 0.01 to 1.2% by weight added to Fe of 52 to 61% purity. Furthermore, a zirconium alloy means the one comprising any one or more of Hf of 0.005 to 10%, Nb of 0 to 4%, Sn of 0 to 3%, Mo of 0 to 2%, Fe of 0.1 to 1%, Cr of 0 to 1%, Ni of 0 to 0.1%, Cu of 0 to 0.1% by weight added to Zr of 90 to 98.5% of purity.

A metal oxide layer of metal implants according to the present invention is preferred to be 3 nm to 20 μm thick. The thickness of less than 3 nm is not desirable due to less than that of automatically oxidized film. In case of over 20 thereof, the oxide layer is very brittle leading to cracking, peeling and the like during long period of implants in the living body, which is not desirable as the cause of biomedical foreign body reaction.

Said metal oxide layer as described later, any one or more methods of automatically forming by reacting with oxygen in the air after mechanical processing, forming by anode reaction in an electrolyte, and forming by heat treating in the air or in the atmosphere of plasma may be possible.

In case said metal oxide layer is automatically formed by oxidized reaction with air, the thickness thereof is 3 to 20 nm.

In case said metal oxide layer is formed by anode reaction in electrolyte, the layer has a double structure composed of a barrier type porous oxidized coated film which thickness is 50 nm to 20 μm.

Said bio-active material according to the present invention means a material suitable to biocompatibility as adding on the surface of the metal implant surface by surface engineering. The term of biocompatibility in the field of bio-active material means a function maintaining without any side effects or toxicity while the material or system functions in a living body. In general, the biocompatibility is classified into two as follows: i) bioinert property: a property attaching to the living tissue by a morphological fixation only, without any toxicity or side effects and without combining with tissue cells in a living body, and ii) bioactive property: a property capable of bioactive fixation without any negative reaction to the living tissue. A living-active material according to the present invention means a bioactive material. The present invention relates to the implants with a characteristic inducing a biochemical bonding eventually by adding a bioactive material leading to increase reactivity with the tissue, and producing thereof.

The bio-active material forming an implanted layer of a bio-active material has to be determined suitably considering the condition of the patient, operated portion, bone density. For example, as a bio-active material capable of inducing a high bioactivity and bone bonding, any alloy composed of any one of Li, Na, K, Rb, Cs, Fr, Mg, Ca, Sr, Ba, Ra, Sc, Y, Lu, Ti, Zr, Hf, Nb, Ta, Cr, Mo, W, Mn, Re, Fe, Ru, Os, Co, Rh, Ir, Ni, Pd, Pt, Cu, Ag, Au, Zn, Ga, In, Ti, Sn, Bi and an alloy of combination thereof may be applied. As the eventual purpose of the present invention is to induce a biochemical bonding not by the previous mechanical bonding but by the surface control of a bio-active material for the bone tissue and the implant-surface, it is very critical to choose said bio-active material.

The thickness of layer for said bio-active material is preferably 1 nm to 3 μm. In the case of less than 1 nm thick, it is not desirable as the quantity of the bio-active material required for inducing a biochemical bonding with a living body according to the present invention. In the case of over 3 m thick, it is not desirable because a considerable amount of the surface erosion occurs as it takes a longer time for injecting the bio-active material, and eventually, the previously injected material is eliminated. The method of producing Osseo-inductive metal implants for a living body according to the present invention comprises the following steps:

(1) forming a layer of metal oxide on the surface of mechanically processed metal implant;

(2) plasma-cleaning the surface of the layer of metal oxide formed in said step (1);

(3) forming a layer of the bio-active material by implanting the ionized bio-active material into the surface of said layer of metal oxide.

As for said step (1) of mechanical processing the metal implant, any one of Ti of the commercial purity, cobalt-chromium alloy, stainless steel and zirconium alloy is to be mechanically processed in a desired form, wherein any method well known in the art for mechanical processing may be applied.

For said step (1), the methods how to form the layer of the metal oxide on the surface of the metal implant mechanical processed are said are as follows:

(a) As titanium, cobalt, chromium and zirconium have very high activity, the layer of metal oxide such as $TiO_2$, $Co_2O_3$, $Cr_2O_3$ and $ZrO_2$ is automatically formed by reacting with oxygen in the air just after mechanical processing thereof. The thickness of the oxide is different depending on the method of mechanical processing, the used coolant, the surface roughness, the method of sterilization. However, it is desirable to maintain the thickness within the range of 3 to 20 nm.

(b) The thickness of the metal oxide layer is increased when increasing electric voltage step by step and making anodic reaction in any one electrolyte or mixed solution thereof out of sulfuric acid, oxalate, phosphoric acid, chrome chloride, acetic acid of 2 to 25% each by weight. The type of the formed metal oxide layer is essentially that of barrier, wherein as comparatively thin and compact layer of the barrier on the boundary surface between the metal and metal oxide, and the coated film of the dielectric are destroyed in accordance with the voltage increase leading to form a double structure composed of irregular and thick porous anodic oxidized film. In the case of such method, as for the concentration of the solution, electric density and voltage, it requires to choose the optimized condition thereof unless any cracks occur in the layer of the oxide. Furthermore, it may be also possible to add calcium chloride dehydrate, buffer solution (HEPES), sodium phosphate and the like to said solution to induce precipitated calcium phosphate in the layer of oxide. If required, to plan sterilizing and crystallizing, recrystallizing of the oxide layer, water pressure heat treatment may be possible under pressure of 1 MPa or more at 50 to 300 μm. If the temperature is less than 50° C., it is not preferable because the sterilization and the recrystallizing of the oxide layer can not be performed. If the temperature is over 300° C., it is not desirable because there may be danger such as thermal strain and crack during shrinking. If the pressure is less than 1 MPa, it is not also desirable because penetrating depth is insignificant by which sterilization on the porous surface is not sufficiently carried out.

(c) A uniform and compact layer of the metal oxide is formed when a mechanical processed metal implant is heated in the air or in the plasma atmosphere at 150 to 1300° C. If less than 150° C., it is not desirable because the speed of oxide film forming is very slow. If more than 1300° C., it is not also desirable because it approaches the melting temperature leading to heat distortion.

(d) The metal oxide layer may be formed by a method combined two or more of said (a) to (c).

For said step (2), cleaning to eliminate polluted material and impurities absorbed on the surface of the metal oxide are carried out by two steps of normal wet and dry cleaning. The wet cleaning is performed by degreasing, water cleaning, pickling and the like. For the dry cleaning, plasma cleaning is carried out by mounting the metal implant to the cathode portion of a vacuum chamber mounted to a jig after said wet cleaning. In this case, said plasma cleaning is carried out by using plasma composed of any ion of argon, nitrogen, oxygen or more mixed ions.

As for the plasma cleaning condition, it is appropriate to perform within 1 minute to 1 hour applying 50 to 3000V of DC voltage under pressure of 0.1 to 13.3 Pa. In such case, it may be also possible to apply the DC voltage in a pulse form. If the pressure is less than 0.1 Pa, it is not desirable as the forming of plasma is difficult, if the pressure is over 13.3 Pa, as the cleaning effect is weak due to short average free stroke of the ion, if the voltage is less than 50V, as the impact energy level of the ion is not high, and if over 3000V, as a poor surface is provided by ion damages on the surface respectively.

In said step (3), the surface of metal oxide layer is modified by implanting ionized bio-active material into the surface of the metal oxide, wherein the layer of the metal oxide as the peripheral surface layer is a nuclear element during symphysis, thus, the surface deformation of the metal oxide layer may greatly effect on the biocompatibility and symphysis as cells react directly with the peripheral metal oxide layer for the implant.

The ionized bio-active material used at step (3) is obtainable in a vacuum chamber. As for such ionized methods, all those may be used if they could be ionized in a vacuum chamber. For example, any one of Vacuum Arc, Filtered Vacuum Arc, MEVVA: Metal Vapor Vacuum Arc, Ion plating, CVD: Chemical Vapor Deposition, PACVD: Plasma Assisted Chemical Vapor Deposition, Sputtering, Laser ablation and a combination thereof may be used.

In said step (3), as a method of implanting said ionized bio-active material into the surface of the metal oxide by applying electrical energy, any one of Beamline Ion Implantation, PSII:Plasma Source Ion Implantation, MePIII&D: Metal Plasma Immersion Ion Implantation, Deposition and a combination thereof may be used.

On this occasion, it is desirable to implant the ionized bio-active material on the surface of the metal oxide layer heating at 15 to 600° C. If less than 15 μm, it is not desirable as the implant has to be cooled additionally, and is also the same if over 600° C., as the internal diffusion of the impregnated material occurs.

Then, it is preferably to hold 1 KeV to 1 MeV as for an ion implanted energy, $1 \times 10^{13}$ to $1 \times 10^{18}$ ions/cm$^2$ as for an ionized implanted amount. If the ionized implanted energy is less than 1 KeV, it is not desirable as etching occurs in advance rather than the ionized implant, on the other hand, if over 1 MeV, it is also not desirable as a biochemical bonding at the boundary has difficulty due to too deep implanting depth. Also, if the ionized implant amount is less than $1 \times 10^{13}$ ions/cm$^2$ it is not desirable as the metal or the metal oxide layer loses their characteristics due to excessive implanted material.

The method of producing Osseo-inductive metal implants for a living body may comprise additional step of post treatment further after the implant treatment of the ionized bio-active material for said step (3), wherein there are a heat treating method such as heating in the air, in a vacuum, a hydrothermal treating method, dipping method in any one or more mixed solution of hydroxy apatite, calcium, phosphoric acid, or any one or more combined treating method out of heating at 25 to 300° C. under state of deepening in said solution or ultrasonic vibration. The post treatment may also be omitted.

The Osseo-inductive metal implants produced by said method according to the present invention may be applied usefully in the fields of dentistry, orthopedic surgery, ENT, mandibulofacial surgery, plastic surgery

MODE FOR THE INVENTION

The present invention is described in details referring to a example as follows, but not limited to the example.

EXAMPLE

Step 1

Forming of the Metal Oxide Layer on the Surface of a Titanium Implant

After cutting and mechanical processing titanium of 98% of purity in the form of disc or implant, the layer of oxide of 5 nm thick was formed on the surface of titanium disc or implant by reacting with oxygen in the air.

Step 2

Elimination of Contaminants

After cleaning the surface of the metal oxide formed at said Step 1 by alkali degreasing solution, further cleaning was carried out by plasma composed of Ar ion for ten minutes under pressure of 10 Pa, and voltage of 300V by providing a cathode portion in a vacuum chamber.

Step 3

Ionization of a Bio-Active Material and Formation of Layer of Bio-Active Material Implanted Ca was ionized by the vacuum arc method. That is, pulse electric current of 200 A was applied to the calcium cathode of 6 mm diameter. Then, the pulse interval was 300 μs, and the frequency was 3 Hz.

Maintaining 25° C. under 40 KeV of ion energy, $5 \times 10^{16}$ ions/cm$^2$ of ion implantation, said ionized calcium was implanted into said layer of titanium oxide to form the bio-active material of 0.1 μm thick.

Step 4

Post Treatment

The titanium obtained at said Step 3 was post treated by heating under steam of 0.1 MPa at 120° C. for 15 minutes.

Comparative Example

By the same method as in said example except without performing step 3, an implant was produced.

Test Example 1

Measurement of Reactivity with a Living Body

Figure 1:
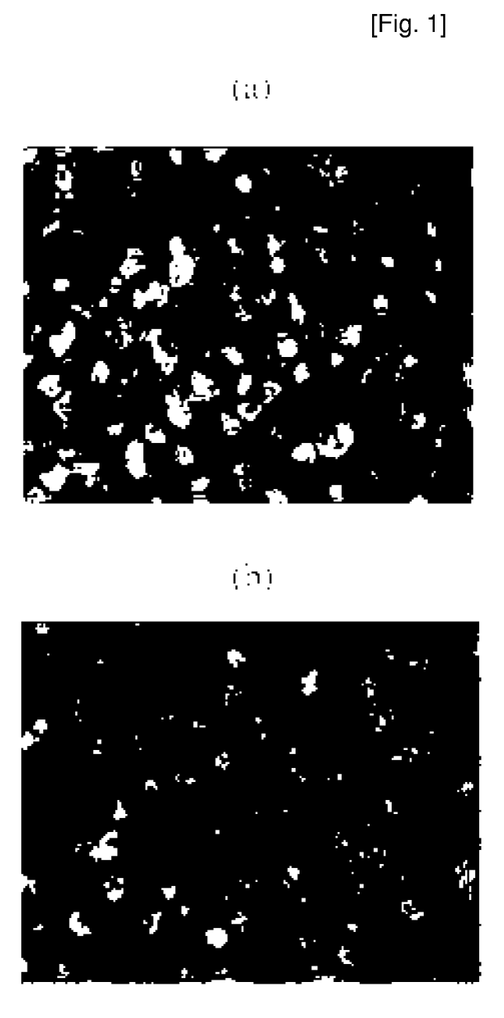
FIG. 1 is a photo comparing reactivity to a living body of a metal implants for an example (FIG. 1a) and a comparative example (FIG. 1b).

To measure reactivity with the living body of the metal implant, the reactivity of KS483 Osteoblast cell on each surface of implants produced by the example and comparative example was observed, which comparison result was shown in FIG. 1.

Said measurements were carried out by the following method:

Each specimen for said example and comparative example respectively was filled in each glass bottle. Then, by 3rd distilled water and ethyl alcohol each was cleaned four times respectively and then moved to a clean bench. Next, washing by the distilled water and UV sterilization were carried out followed by the contamination test for one day. After verifying the contamination, the specimens were transferred to other prepared containers and seeding of cells was carried out. After 3 days of cultivation, dyeing for 20 minutes with neutral red color followed by fixing in 5% formalin each specimen was observed by a fluorescent microscope.

As verified in FIG. 1, total number of cell attachment on the surface of the metal implant made by the example was far more than the number of those made by the comparative example, and the spreading of the cell attachment was also excellent.

This means that the cytoplasmic process and cytodifferentiation of the cell for the osteoblast on the surface of the metal implant made by the example is far better than those of the case made by the comparative example.

Test Example 2

Observation of the Metal Implant Section

Each section of the metal implants made by each example and comparative example was observed by which any existence of compact film without any boundary. According to a perspective view as shown in FIG. 2a, it is found that the metal implant made by the example does not have any clear boundary between a base metal and the layer of implanted material, but assume an aspect which implanted material is distributed to a specified depth (varies depending on the implanted energy and quantity) from the surface.

Figure 2:
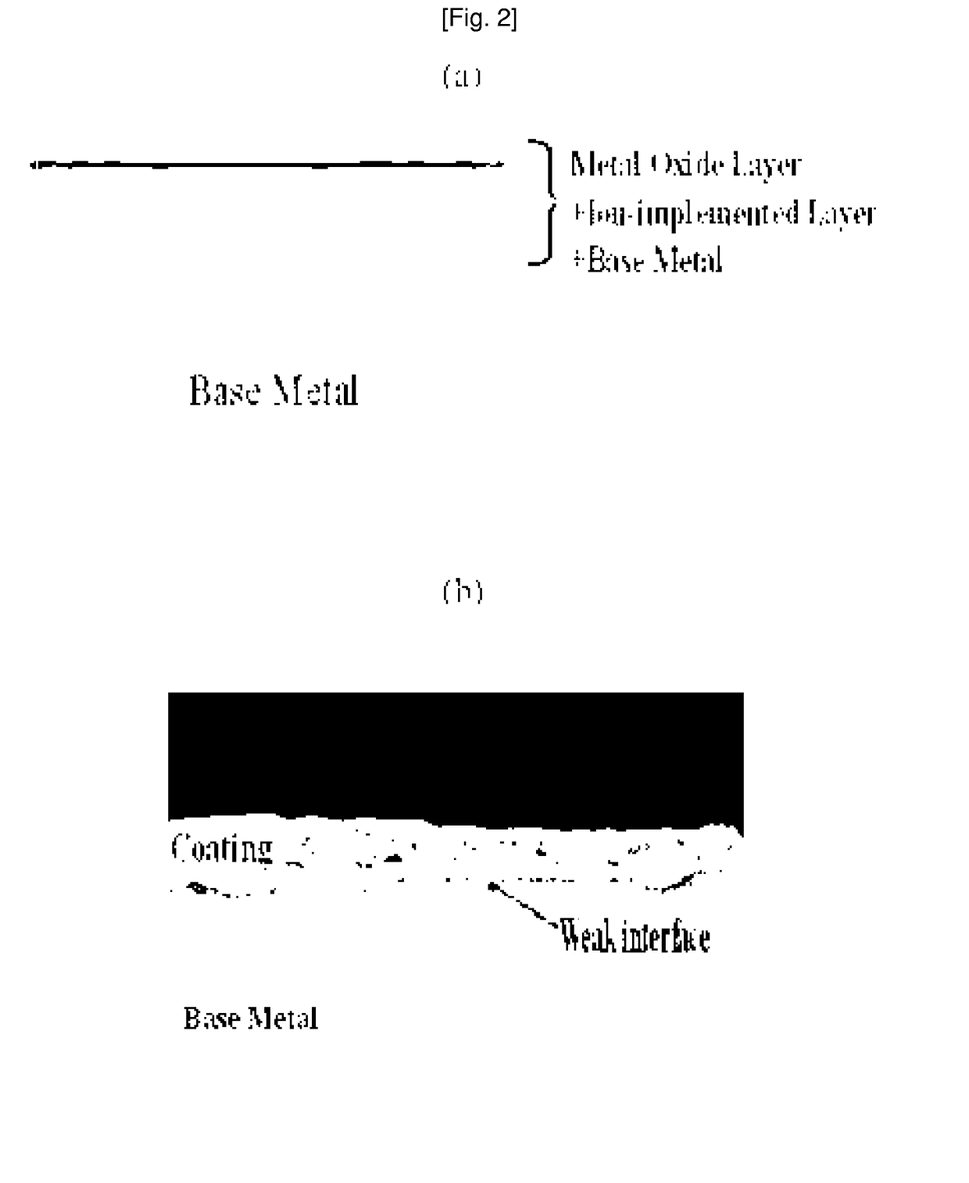
FIG. 2 is a perspective view showing the section of a metal implant for an example (FIG. 2a) and an electron micrograph showing the section of metal implant for a comparative example (FIG. 2b)

As verified in FIG. 2b, the metal implant made by the comparative example has a clear boundary between the base metal and the coating layer. It is not desirable to provoke the inflammation of bone tissues near the implant and the like due to delaminating from the boundary or fine defect of inner part of the coating layer.

Test Example 3

Composition Analysis of the Boundary of the Implant

Figure 3:
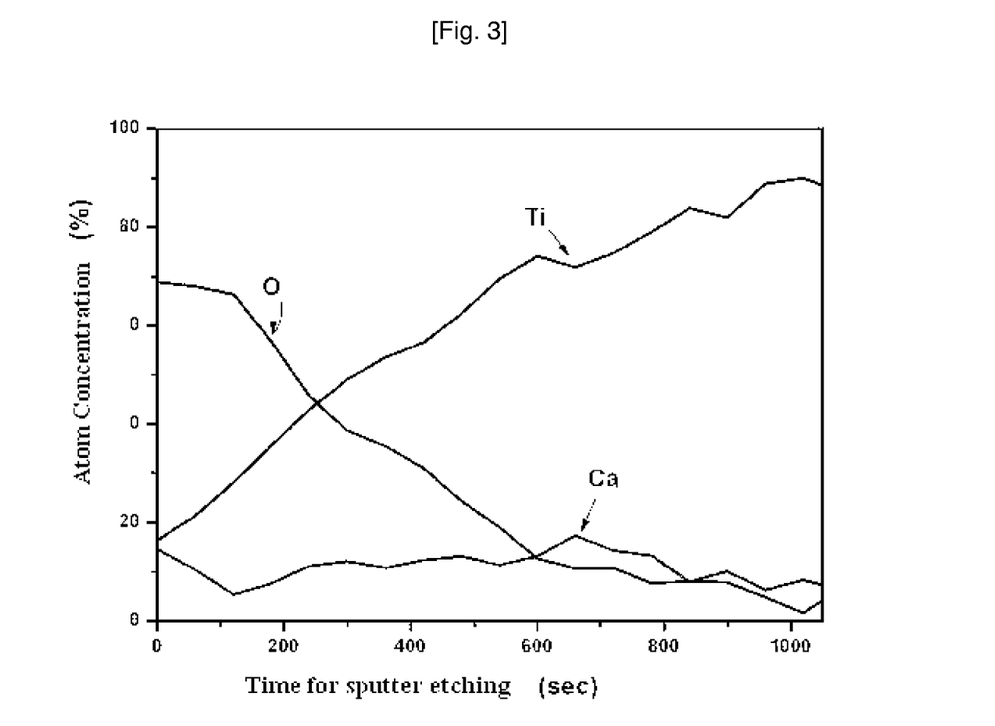
FIG. 3 is a graph showing an Auger depth profile for the boundary of a metal implant for an example.

For the test of the metal implant made by the example, an auger electron spectrometer was used, wherein the analysis of the composition thereof was carried out, sputter etching from the surface toward the depth direction. The result is shown in FIG. 3.

From the surface of said implant to the depth sputter etching for about 250 seconds, a layer of oxide was formed, and thereafter, titanium, a base metal was detected. On the other hand, calcium, from the surface to the depth sputtering etching for about 1000 seconds, was existed within the range of 7 to 17% atom by weight. At sputter etching depth for about 660 seconds, a distribution having a maximum point of 17% atom.

Therefore, the metal implant according to the present invention is characterized in that it has no boundary by forming a bio-active implant layer integrated with a base metal, the delaminating does not occur comparing with the prior arts of coating. As the bio-active material on the surface is integrated with a base material, it is found that it has an excellent advantage of reactivity with a living body at the same time.

Test Example 4

Figure 4:
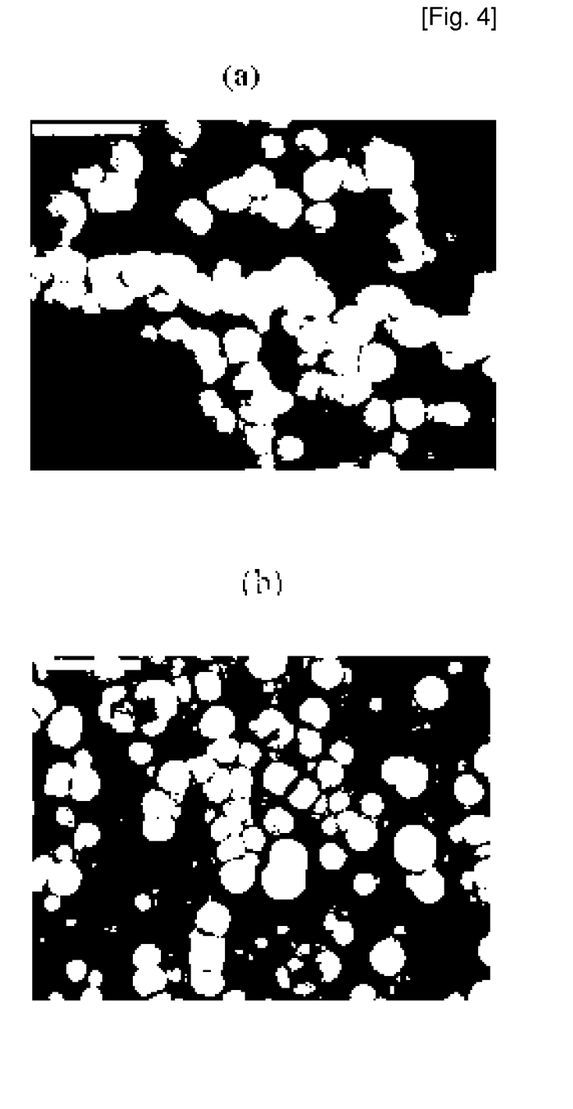
FIG. 4 is scanning electron microscopic photos observed after metal implants of an example (FIG. 4a) and a comparative example (FIG. 4b) were immersed in pseudo body fluid at 36.5° C. for 28 days.
Figure 5:
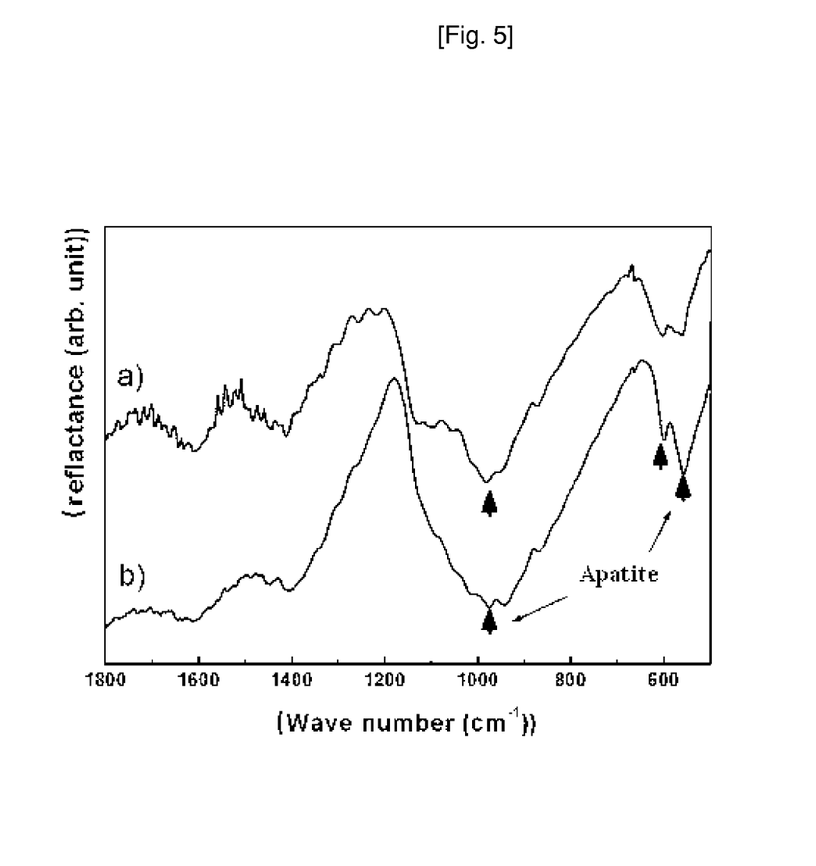
FIG. 5 is a FR-IR graph measured after metal implants of an example (b) and a comparative example (a) were immersed in a pseudo body fluid for 28 days at 36.5° C.

Comparison of Apatite Formability Between the Working Example and the Comparative Example Each implant made by each example and comparative example was settled down in body blood plasma and SBF, simulated body fluid which inorganic concentration is similar to the plasma for specified period of time, and each apatite formability thereof was measured. The results are shown in FIG. 4 and FIG. 5. The apatite as a material composed of Ca and P is known as the precursor of hydroxyapatite, a major component of the bone.

FIG. 4 is scanning microscopic photos observed after the example (FIG. 4a) and the comparative example (FIG. 4b) were settled down in SBF at 36.5° C. for 28 days. In the case of the comparative example, it is found that particles of small bulb shape were formed on the surface, meanwhile, in the case of the example, leaf like particles were formed on the surface, which size or density was considerably increased comparing over the comparative example. Furthermore, it can be seen that particles contacted mutually to be interconnected.

To observe each phase formed on each surface of the implants of example and comparative example, FT-IR analysis was carried out, which result is shown in FIG. 5. According to FIG. 5, the phase of the particles formed on the surface is composed of apatite. It can be verified that the formation of the apatite was promoted by the implanted calcium ion.

As the implant according to the present invention through Test example 4 promotes the formation of apatite, it can be found that it not only reacted faster and excellent osteogenesis when being inserted into the human body but also the healing time could be reduced.

Test Example 5

Symphysis Reaction Tests for the Example and Comparative Example

Figure 6:
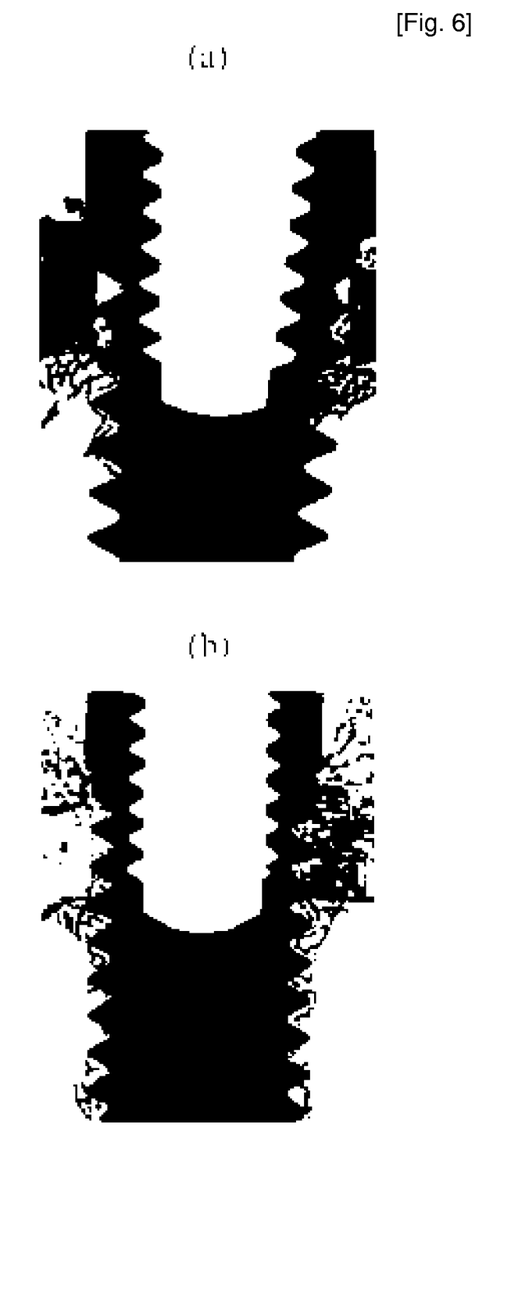
FIG. 6 is reactive test results for the symphysises of an example (FIG. 6a) and a comparative example (FIG. 6b).

To compare the symphysis reaction for the implant made by the example and comparative example, each implant was implanted to a healthy white rabbit from New Zealand. Each implant was carried out in each left and right shank located below about 10 mm from each knee joint. After three weeks elapsed since each implant was performed, the specimens were collected from the rabbit. Then, after fixing and dehydration thereof, Observations based on the tectology which results are shown in FIG. 6a (example) and FIG. 6b (comparative example) were made.

In view of an assessment result based on the tectology, the implant made by example was more excellent than that made by the comparative example not only in newly formed bone near the cortical bone but also in the speed of new bone formation for the edosteal new bone formation of subcotex and the amount of new bone formation.

INDUSTRIAL APPLICABILITY

The metal which bio-active material is implanted, in particular, titanium/titanium alloy and cobalt-chromium alloy, stainless steel (314, 316, 316L, and 22-13-5 Stainless Steel) and zirconium alloy implants are a total sum of Osseo-inductive metal implant for bio-active material and control technology for surface components, wherein reactivity with a living body is excellent and compact film without any boundary is formed leading to generate a biochemical layer without any degradation and peeling, as the synotosis of the implant and the biomass due to such biochemical combination and the healing time becomes faster, it may be applied usefully as a medical device for implanting bio masses for dentistry, orthopedic surgery, mandibulofacial surgery, surgical operation and veterinary surgical operation and the like.

The invention claimed is:

1. A method of producing a metal implant for a living body, the method comprising:
   mechanically processing a titanium alloy to form a metal implant substrate;
   forming a titanium oxide layer on a surface of the processed metal implant substrate with a thickness of 3 nm to 20 nm;
   cleaning a surface of the titanium oxide layer on the metal implant substrate in an alkali degreasing solution;
   cleaning the titanium oxide layer of the metal implant substrate in a plasma atmosphere;
   ionizing a bio-active material selected from a group of consisting of Li, Na, Mg and Ca; and
   implanting the ionized bio-active material on the surface of the plasma cleaned titanium oxide layer of the metal implant substrate,
   wherein the ionized bio-active material is implanted on the surface of the plasma cleaned titanium oxide layer with 40 KeV of ion energy,
   wherein the ionized bio-active material is implanted while maintaining a temperature of the plasma cleaned titanium oxide layer at 25° C., and
   wherein the ionized bio-active material is implanted to form a bio-active material layer having a thickness of 0.1 µm.

2. The method of producing the metal implant for a living body of claim 1, wherein the titanium oxide layer on the metal implant substrate is formed by oxidation in an air atmosphere.

3. The method of producing the metal implant for a living body of claim 2, wherein the cleaning in the plasma atmosphere is performed with Ar ion plasma for ten minutes under a pressure of 10 Pa, and a voltage of 300V by providing a cathode reaction in a vacuum chamber.

4. The method of producing the metal implant for a living body of claim 1, wherein the bio-active material layer is formed between the titanium oxide layer and the metal implant substrate.

5. The method of producing the metal implant for a living body of claim 1, wherein the bio-active material is Ca.

6. The method of producing the metal implant for a living body of claim 1, wherein the bio-active material is Mg.

7. The method of producing the metal implant for a living body of claim 1, wherein the cleaning in the plasma atmosphere is performed with Ar ion plasma for ten minutes under a pressure of 10 Pa, and a voltage of 300V by providing a cathode reaction in a vacuum chamber.

* * * * *